United States Patent
Minfelde et al.

(10) Patent No.: US 6,755,830 B2
(45) Date of Patent: Jun. 29, 2004

(54) CONNECTOR FOR A SPINAL FIXATION MEMBER

(75) Inventors: Richard Minfelde, Paris (FR); Jean-Francois D'Amore, Montervrain (FR); Philippe Dupont, Claye Souilly (FR)

(73) Assignee: Sofamor S.N.C., Cedex (FR)

( * ) Notice: Subject to any disclaimer, the term of this patent is extended or adjusted under 35 U.S.C. 154(b) by 4 days.

(21) Appl. No.: 10/190,327

(22) Filed: Jul. 5, 2002

(65) Prior Publication Data

US 2003/0045879 A1 Mar. 6, 2003

(30) Foreign Application Priority Data

Jul. 4, 2001 (FR) .............................................. 01 08892

(51) Int. Cl.⁷ .......................... A61B 17/70; A61B 17/86
(52) U.S. Cl. .......................................... 606/61; 606/73
(58) Field of Search .............................. 606/53, 54, 60, 606/61, 72, 73, 104; 623/17.11, 17.14; 403/294, 387, 395, 396, 400; 248/65, 70, 71, 73

(56) References Cited

U.S. PATENT DOCUMENTS

| | | | |
|---|---|---|---|
| 5,209,752 A | 5/1993 | Ashman et al. | |
| 5,254,118 A | * 10/1993 | Mirkovic | 606/61 |
| 5,306,275 A | 4/1994 | Bryan | |
| 5,312,404 A | 5/1994 | Asher et al. | |
| 5,344,422 A | 9/1994 | Frigg | |
| 5,380,325 A | 1/1995 | Lahille et al. | |
| 5,403,314 A | 4/1995 | Currier | |
| 5,429,639 A | * 7/1995 | Judet | 606/61 |
| 5,466,237 A | 11/1995 | Byrd, III et al. | |
| 5,474,551 A | 12/1995 | Finn et al. | |
| 5,476,463 A | 12/1995 | Boachie-Adjei et al. | |
| 5,527,314 A | 6/1996 | Brumfield et al. | |
| 5,534,002 A | 7/1996 | Brumfield et al. | |
| 5,540,688 A | * 7/1996 | Navas | 606/61 |
| 5,562,662 A | 10/1996 | Brumfield et al. | |
| 5,667,508 A | * 9/1997 | Errico et al. | 606/73 |
| 5,676,665 A | 10/1997 | Bryan | |
| 5,741,255 A | 4/1998 | Krag et al. | |
| 5,876,403 A | 3/1999 | Shitoto | |
| 6,022,350 A | * 2/2000 | Ganem | 606/61 |
| 6,443,953 B1 | * 9/2002 | Perra et al. | 606/61 |
| 6,551,318 B1 | * 4/2003 | Stahurski | 606/61 |
| 2002/0111626 A1 | * 8/2002 | Ralph et al. | 606/61 |

FOREIGN PATENT DOCUMENTS

WO    WO 01/10317 A1    2/2001

* cited by examiner

Primary Examiner—Kevin Shaver
Assistant Examiner—David C. Comstock
(74) Attorney, Agent, or Firm—Woodard, Emhardt, Moriarty, McNett & Henry LLP

(57) ABSTRACT

Lateral connector with adjustable offset for a connection between a rod and a member for fixation to the spine, comprising a component to be connected to the fixation member and provided with an extension inserted into a second component which comprises a seat for the rod and a way to immobilize the rod and the extension when placed in contact with each other. The first component comprises a head with an opening with a bearing surface of articulation cooperating with a corresponding bearing surface of the fixation member. The second component comprises an orifice for receiving the extension, permitting rotation of the second component about the extension, with the orifice intersecting the bottom of the seat to form a slot.

20 Claims, 2 Drawing Sheets

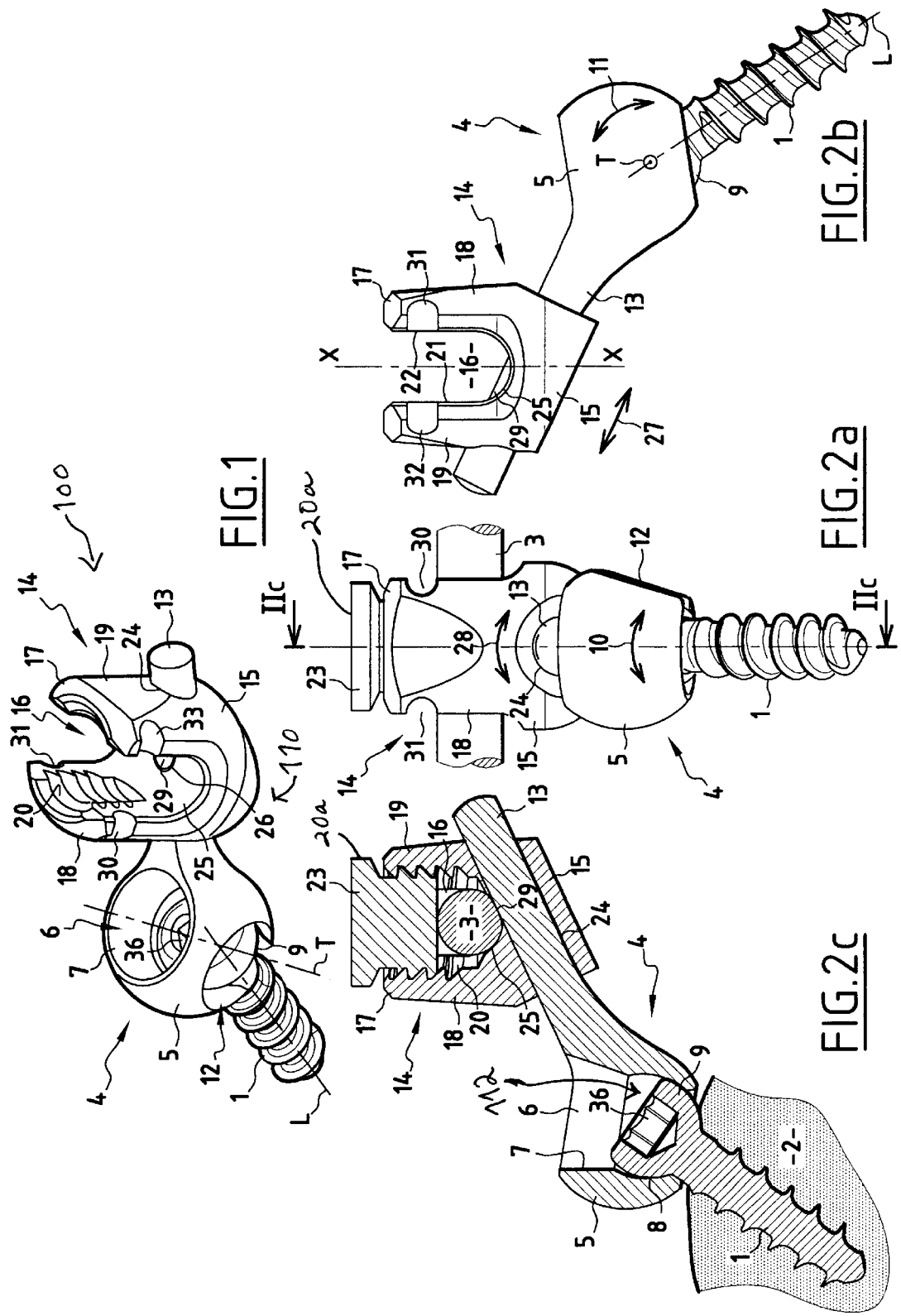

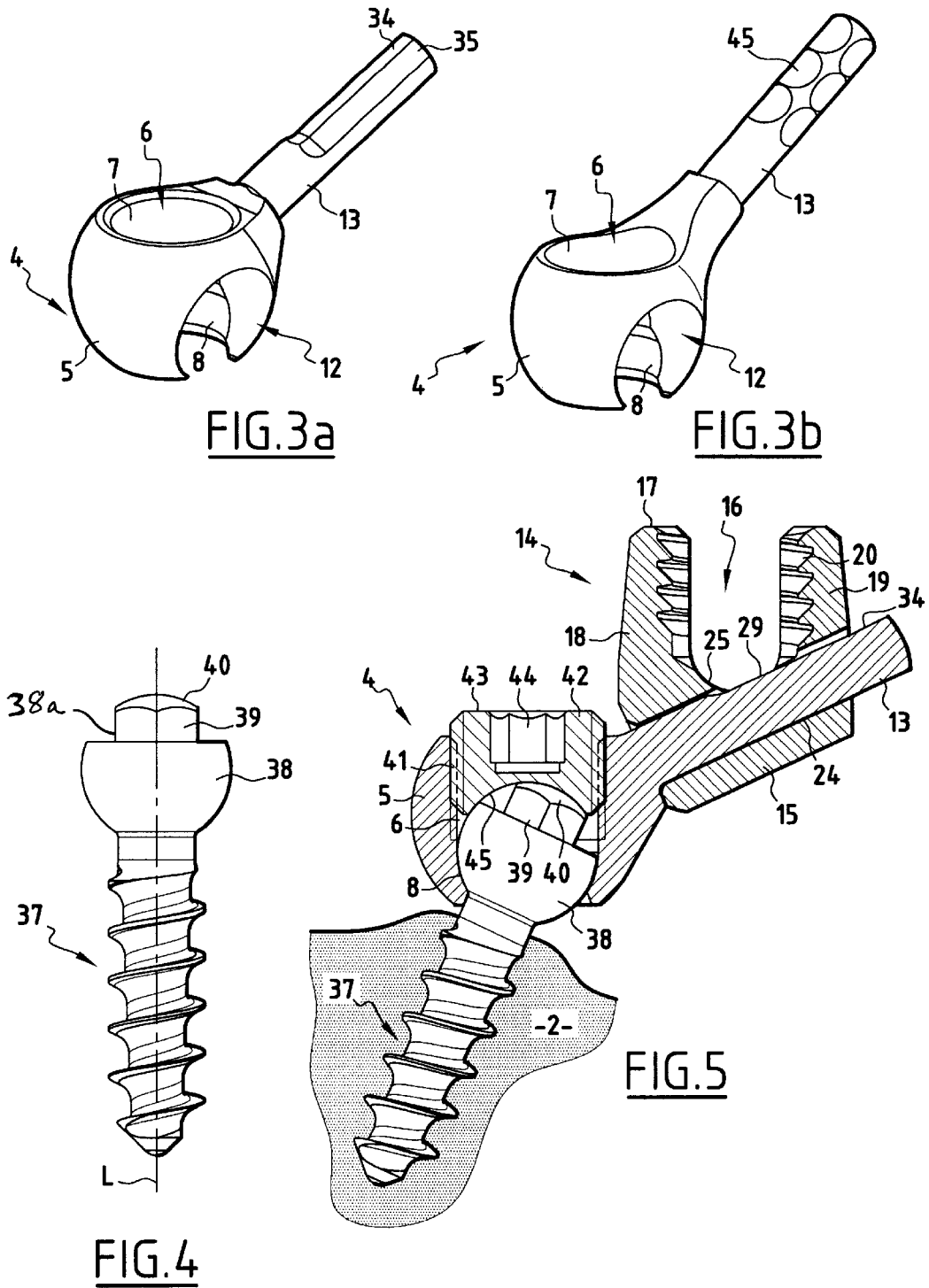

CONNECTOR FOR A SPINAL FIXATION MEMBER

BACKGROUND

The invention relates to implants for devices intended for stabilizing the spine.

Devices intended for correcting deformations of the spine and for stabilizing it comprise metal rods which extend along the spine and pass through orifices formed in one end of connection elements which are themselves fastened to the vertebrae via their other end, shaped like a hook, or are screwed into these vertebrae via a threaded end. The rod is immobilized inside the orifice, for example by means of a threaded plug.

In some cases, the orifice through which the rod passes is situated substantially in the continuation of the longitudinal axis of the connection element. In other cases, the connection element is configured in such a way as to laterally offset the longitudinal axis of the connection element relative to the orifice passed through by the rod. This element is then referred to by the term "lateral offset connector".

The document U.S. Pat. No. 5,476,463 describes such a lateral connector with lateral offset. It is made up of a one-piece component comprising a head through which the rod is intended to pass and is connected to a lateral stem provided with an oblong opening intended to be passed through by a screw implanted in a vertebra. In this type of connector, the orientation of the stem in relation to the head is fixed by construction and cannot be modified. To obtain an implantation of the connection elements approximating to the desired optimum, it is therefore necessary for the surgeon to have a range of connectors available whose stems have different orientations and lengths. The need to select them one by one slows down the implantation of the correction device. Moreover, the inevitable limitation on the number of orientations and lengths available for the lateral stem does not always permit optimum implantation of the connection element on the vertebrae. In particular, the site of fixation of the connection element may not always be the one which is the most favourable to the patient. This is especially true when the correction device is implanted in the cervical area, where the vertebrae are small and have a tortuous shape, leaving few locations favourable to the fixation of an implant, particularly of a screw.

Moreover, some devices of the type described above only permit positioning of the connection screw after the connector has been placed on the rod. The site of fixation of the screw is thus completely forced on the surgeon, which makes fitting awkward and often inappropriate to the anatomy of the patient.

It has been proposed, as in document U.S. Pat. No. 5,534,002, to form lateral offset connectors in two parts. The first part is made up of a component intended to be passed through, on the one hand, by the rod and, on the other hand, by an end of a lateral stem constituting the second part of the connector and of which the other end has an opening intended to be passed through by a fixation screw. The engagement of the lateral stem in the component can be controlled by the surgeon, and the member for immobilizing the rod in the component also acts in such a way as to press the rod and the stem together against the component to definitively fix their relative positions. This type of lateral connector with adjustable offset does not permit control of the angular position of the stem in relation to the rod, no more than a rotation of the stem in the head, the stem being of partially rectangular cross section. Moreover, in practice, there is no possibility of placing the connection screw in the vertebra after the connector has been positioned on the rod: it often happens that it is necessary to leave part of the screw protruding from the vertebra, which increases the size of the device needlessly and dangerously.

SUMMARY

It is an object of the invention to make available to surgeons a type of lateral connector with adjustable offset for a device for stabilizing the spine, connecting a rod and a means for fixing the connector to a vertebra which is quick and easy to fit at any point of the spine, including in the cervical area, and permitting optimum placement of the fixation means under all conditions.

To this end, the subject of the invention is a lateral connector with adjustable offset for providing a connection between a rod of a device for correcting and stabilizing the spine and a fixation member for fixing said device to the spine, such as a screw or a hook, of the type comprising a first component intended to be connected to said fixation member and provided with an extension intended to be inserted in translation into a second component of said connector, said second component being formed by a head which comprises a seat for receiving said rod and means for immobilizing said rod in said seat, said immobilizing means also immobilizing the extension in the second component, characterized in that:

said first component comprises a head provided with an opening which passes right through it and whose lower part has a bearing surface of articulation intended to cooperate with a corresponding bearing surface formed on a head of said fixation member, said extension having a generally cylindrical shape; and in that said second component comprises an orifice formed in said head for receiving the extension of the first component and permitting a rotation of said second component about the extension, said orifice having an intersection with the bottom of the seat in such a way as to form a slot there, so that a portion of the lateral surface of the extension in the position of insertion protrudes inside the seat.

The head of the first component preferably comprises a lateral aperture allowing said head of the fixation member to be inserted into said opening.

The axis of the seat receiving the rod and the orifice receiving the extension of the first component are preferably oriented obliquely in relation to one another.

Said extension can comprise an at least partially polygonal section forming longitudinal flats on its lateral surface.

Said extension can comprise transverse recesses whose shape matches that of the outer surface of the rod.

Said extension can have a knurled finish on its lateral surface.

Said means for immobilizing the rod in the second component can be formed by a threaded plug cooperating with a thread formed in the head of the second component.

Said head of the second component can have two lateral branches delimiting the seat, the latter being open on the upper face of the head.

The connector according to the invention can comprise means for immobilizing said first component relative to said fixation member.

The opening in said first component can be formed, in its upper part, by an internally threaded hole, and said immobilizing means can be formed by an externally threaded plug.

The invention also relates to an assembly formed by a connector as described above and by a fixation member intended to be implanted on the spine and cooperate with said connector.

Said fixation member intended to be implanted on the spine and adapted to cooperate with a connector for a device for correcting and stabilizing the spine, linking it to a rod, of the type with a spherical head, can be such that said head has, on its upper part, an extension whose upper surface is of spherical shape. Its lower part can be formed by a screw or a hook.

The assembly formed by a connector according to the invention and a fixation member is then such that the plug of the first component has, on its lower face, a spherical bearing surface cooperating with the upper surface of the fixation member.

In another aspect of the present invention, an adjustable lateral connector is provided with two separate components configured in the manner described. The first component comprises a head forming a receiver, in the bottom of which is intended to be placed the head of a fixation member, such as a screw, already anchored or intended to be anchored on a vertebra. The bottom of the receiver and the head of the fixation member are configured in such a way as to allow an articulation of these two components relative to one another in the manner of a ball and socket joint. The head of the first component comprises an extension of substantially cylindrical shape intended to be inserted into the second component of the connector. This second component comprises a head forming a receiver in which is intended to be inserted a substantially cylindrical rod of a device for stabilizing the spine. A threaded plug or any other similar means presses the rod against the bottom of the receiver. The head of the second component comprises an orifice in which the cylindrical extension of the first component is inserted by sliding. This orifice is formed in such a way that a fraction of the surface of the extension, after positioning, opens into the receiver. Thus, the rod of the stabilizing device, when it is pressed against the bottom of the receiver, exerts a pressure on the extension which keeps it in the orifice, at the position chosen by the surgeon. For optimum choice of this position, the surgeon can modify the engagement of the extension in the orifice, which determines the distance between the heads of the first and second components of the connector, and also the angle of rotation of the head of the second component about the extension. Since, in addition, the orientation of the first component relative to the head of the fixation member is free on account of the fact that they are articulated on one another (they can, if appropriate, then be made integral with each other at this orientation), the surgeon has the greatest possible latitude for connecting the rod of the spinal stabilizing device to a given vertebra. In particular, he has very great freedom in choosing the site of implantation of the fixation member, which can be of particular interest for the cervical region.

Another embodiment comprises: a rod; a spinal fixation member; a first connector component including a first head defining a first opening therethrough and an elongated extension, which engages the fixation member in a ball and socket joint arrangement; a second connector component including a second head defining a seat to receive the rod and an orifice intersecting said seat to receive the extension; and a fastener to fix said extension and said rod in contact with one another in said second head.

Yet a further embodiment includes a method, comprising: providing a lateral connector including a first component with a first head and an extension, and a second component with a second head defining a seat configured to receive a rod and an orifice intersecting the seat; implanting a fixation member in a spine of the patient; receiving the fixation member in the first head; adjusting position of the first component about the fixation member after said receiving in a first direction of rotational freedom; inserting the extension into the orifice of the second component; translationally adjusting distance between the first head and the second head after said inserting; rotationally adjusting the second head about the extension after said inserting; and fixing the extension and the rod in contact with one another in the second head of the second component.

Alternatively or additionally, this method further includes:

changing position of the first component about the fixation member after said receiving in a second direction of rotational freedom different than the first direction of rotational freedom; removing an end portion of the extension after said inserting; and/or immobilizing the fixation member with respect to the first head after said adjusting and said changing.

In still another form of this method, receiving the fixation member includes engaging an articulating surface of the first head with a spherical surface of the fixation member and the fixation member includes a tooling extension projecting away from said spherical surface, the tooling extension terminating in a spherically shaped upper surface, and wherein said immobilizing includes threading a plug into an opening of the first head to contact the upper surface of the tooling extension.

In yet another form of this method, implantation of the fixation member is performed before receiving it, and the first head includes an opening therethrough intersected by a lateral notch to receive the fixation member by laterally sliding an upper head portion of the fixation member into the first head through the lateral notch.

Further embodiments, objects, features, benefits, advantages, aspects, and forms of the present invention shall become apparent from the description and figures provided herewith.

BREIF DESCRIPTION OF THE DRAWING

The invention will be better understood on reading the following description in which reference is made to the attached figures, where:

FIG. 1 shows a perspective view of a lateral connector with adjustable offset according to the invention, mounted on a screw for anchoring in a vertebra;

FIGS. 2a, 2b, and 2c show a front view (FIG. 2a), a side view (FIG. 2b) and a cross section along IIc—IIc (FIG. 2c) of this same connector and this same anchoring screw; FIG. 2c also shows the rod of the device for stabilizing the spine and the threaded plug which holds it on the connector, as well as the vertebra in which the anchoring screw is fixed;

FIGS. 3a and 3b show perspective views of two alternative embodiments of the first component of a connector according to the invention;

FIG. 4 shows a front view of an example of an anchoring screw adapted to an alternative embodiment of the connector according to the invention;

FIG. 5 shows, in a cross section identically to the connector in FIGS. 2a–2c, an alternative embodiment of the connector according to the invention using the screw from FIG. 4.

DESCRIPTION OF SELECTED EMBODIMENTS

For the purposes of promoting an understanding of the principles of the inventions, reference will now be made to the embodiments illustrated in the drawings and specific language will be used to describe the same. It will nevertheless be understood that no limitation of the scope of the inventions is thereby intended. Any alterations and further modifications of the principles of the inventions as illustrated or described herein are contemplated as would normally occur to one skilled in the art to which the inventions relate.

Referring to FIGS. 1, 2a, 2b, and 2c; a spinal stabilization device 100 including lateral connector 110 is illustrated. The lateral connector 110 with adjustable offset according to one embodiment of the invention is intended to connect a fixation member implanted on the spine, such as a screw 1 implanted in a vertebra 2, to a rod 3 of a device for stabilizing a region of the spine. This connector 110 is made up of two separate components.

The first component 4 comprises, in the first place, a head 5 which has an opening 6 passing through it. The inner wall 7 of the head 5 has, in its lower part, a concave bearing surface 8, of generally spherical shape in the example shown, which is intended to cooperate with head 9 of the screw 1, the convex shape of which corresponds to it in such a way as to permit articulation of the head 5 of the first component 4 on the head 9 of the screw 1 to provide a ball and socket joint 112 form of engagement. It is thus possible to combine a wide angular range of rotational movement of the first component 4 about the longitudinal axis (L) of the screw 1 (according to the arrow 10) with a wide angular range of tilting movement of the first component 4 about a transverse axis (T) of the head 9 of the screw 1 (according to the arrow 11). The first component 4 of the connector and the screw 1 can thus be oriented relative to one another about two different degrees of rotational freedom. The head 5 of the first component 4 also comprises a lateral notch 12 which opens into the opening 6. This notch 12 has the function of permitting insertion of the head 9 of the screw 1 into the opening 6 in a lateral manner. Accordingly, with this configuration it is possible to fit the first component 4 on the head 9 of the screw 1 after the screw 1 has been fixed in the vertebra 2, this fixation being realized at the site and at the orientation most favorable to the patient.

It would however still be within the spirit of the invention to omit this notch 12, which would entail having to insert the screw 1 into the opening 6 before fixing the screw 1 in the vertebra 2.

The first component 4 also has, on its head 5, an extension 13 of generally cylindrical and elongate shape, that can be oriented in any way relative to the head 5.

The second component 14 of the connector is made up of a head 15 having a seat 16 whose general shape is that of a cylinder of axis (XX) intended to receive a rod 3 of the stabilizing device. In the example described and shown (which is not restrictive, as this head 15 and its seat 16 can have any known shape permitting the function of receiving and fixing the rod 3), the seat 16 is open on the upper surface 17 of the head 15 in such a way as to permit vertical insertion of the rod 3 into the seat 16 without first having to insert the second component 14 on the rod 3 before putting the rod 3 in place. The head 15 thus comprises, in this example, two lateral branches 18, 19 delimiting and defining the seat 16. These lateral branches 18, 19 are configured in such a way as to allow means for immobilizing the rod 3 to be inserted into and held in the seat 16. In the example shown, a thread 20 is provided on the inner faces 21, 22 of the lateral branches 18, 19 in order to receive fastener 20a in the form of a threaded plug 23 (shown in FIGS. 2a and 2c only), which is one of the means for immobilizing the rod 3 which are customarily used on the connectors of devices for stabilizing the spine.

The head 15 of the second component 14 also comprises an orifice 24 which passes right through it, having an intersection with the bottom 25 of the seat 16 for the rod 3, in such a way as to form a slot 26 there. The orifice 24 is adapted to receive the cylindrical extension 13 of the first component 4 with just enough play to permit translation of the second component 14 along the extension 13 in the direction of the arrow 27 and a rotation of the second component 14 about the extension 13 in the direction of the arrow 28. When the extension 13 is in place in the orifice 24, a portion 29 of its lateral surface protrudes inside the seat 16, via the slot 26. Thus, this portion 29 of the extension 13 constitutes a zone of contact with the rod 3 when the latter is fitted in the seat 16. When the immobilizing means such as the plug 23 exert a pressure on the rod 3 in order to keep it fixed in the seat 16, this pressure is transmitted to the extension 13 in such a way as to immobilize it in translation and in rotation inside the orifice 24. Once the plug 23 has been tightened, the relative positions of the rod 3, the first component 4 of the connector and the second component 14 of the connector are fixed. The device for stabilizing the spine is thus made rigid at this area of its fixation to the spine, and in a configuration provided by the geometry of the site of implantation of the connector 110, typically without the surgeon being forced to look for an acceptable and generally imperfect match between the geometry of the implantation site and a connector geometry fixed in advance. If appropriate, this rigid setting can be added to by immobilizing the position of the head 9 of the screw 1 in the head 5 of the first component 4 of the connector, for example by inserting an immobilizing plug into the opening 6 of the head 5, or by a device using a blade forming a spring. An example of such immobilizing by means of an immobilizing plug will be described below.

It will be noted that, in the example shown, the extension 13 and the axis (XX) of the seat 16 are not oriented perpendicularly to one another, but obliquely, which can be particularly desirable to implants in the cervical region. Nonetheless, this characteristic is not compulsory, even for cervical applications.

The head 15 of the second component 14 is configured in such a way as to limit its size without compromising its rigidity. It preferably comprises, in a known manner, notches 30, 31, 32, 33 allowing it to be gripped by a suitable instrument.

To reduce the final size of the connection device after it has been put in place, the surgeon can, if he so wishes, cut off that part of the extension 13 jutting outside the head 15 of the second component 14. Likewise, the lower part of the head 15 of the second component can be given a truncated shape, as is shown in the figures. This reduction in the size of the device is often desirable for implantation in the cervical region.

Alternatively, the outer surface of the extension 13 can be configured in such a way as to increase its contact surface with the rod 3. As is shown in FIGS. 3a and 5, this can be done by giving this outer surface a cross section which is not strictly cylindrical, but al least partially polygonal (although still inscribed within a circle so as not to compromise the possibilities of rotation of the extension 13 in the orifice 24), in such a way as to form longitudinal flats 34, 35 on the extension 13. It is also possible to provide the surface of the extension 13 with a knurled finish in such a way as to form ridges there which penetrate into the rod 3 during its tightening, if such a knurled finish is not already present on the rod 3. Finally, it is possible to provide a series of transverse recesses 45 on the surface of the extension 13, the shape of these matching that of the outer surface of the rod 3, as is shown in FIG. 3b. However, this has the drawback of limiting the number of possible relative positions in translation and rotation of the two components 4, 14 of the connector. These different features can be combined in alternative embodiments.

As has been stated, it is possible to provide means for immobilizing the relative positions of the head 9 of the screw 1 in the head 5 of the first part 4 of the connector. According to an alternative embodiment of the invention shown in FIGS. 4 and 5, the screw 1, whose head 9 has a polygonal female recess 36 allowing it to be tightened using a male tool, can be replaced by a special screw 37 whose head 38 of spherical shape has, in its upper part 38a, a tooling extension 39, preferably polygonal, allowing it to be tightened using a female tool. This tooling extension 39 has an upper surface 40 of spherical shape. Compared with the variant shown in FIGS. 1 and 2, the variant of the connector according to the invention shown in FIG. 5 differs in that the head 5 of the first component 4 comprises an opening 6 which in its upper part is formed by an internally threaded hole 41, into which an externally threaded plug 42 can be inserted. This plug has, on its upper face 43, a polygonal recess 44 making it possible to tighten the plug 42 using a male tool. As regards the lower face of the plug 42, this has a spherical bearing surface 45 so as to cooperate with the extension 39 of the screw 37 and also, preferably, with the head 38 of the screw 37. In this way, the plug 42 when tightened exerts a pressure on the screw 37 in order to press it against the bearing surface 8 of the first part 4 of the connector, and thereby to immobilize the assembly in the optimum position determined upon implantation of the correcting and stabilizing device. FIG. 5 shows this variant of the invention, which here also includes an extension 13 of the first part 4 of the connector having a flat 34.

All the components which have been described are made in a conventional manner of a biocompatible metal material, for example a stainless steel or a titanium alloy, and have mechanical properties adapted to the functions fulfilled by the different components.

The lateral connector with adjustable offset according to the invention has the following advantages in addition to those which have already been mentioned.

While still involving a small number of components, it makes it possible to fix the rod 3 and connect it to the vertebrae 2 using a single means of fixation, hence in a single movement. This guarantees rapid fixation, thus as short as possible a time for fitting the stabilizing device. Moreover, this type of connector guarantees a fine adaptation of the connection to the anatomy of the patient and to the area of the spine where the device is implanted. This makes the connector according to the invention particularly suitable for use in the cervical area, where a highly adaptive connector geometry is often desired because the cervical vertebrae are relatively small, can have tortuous shapes with relatively few areas suitable for fixation of the screws, and/or it is more difficult to position these without risking damage to vital blood vessels. The possibility of positioning the screws 1 at the most suitable sites, prior to securing them to the connector, is also frequently desirable. Also, rod 3 can typically be put into place without any prior shaping, because the connectors can adapt to the geometry of the rod 3 without the need for any major prior adaptation of the shape of the rod 3 to the site and to the fixed configuration of the connectors.

Alternatively, the screw 1 can be replaced by another means of anchoring the connector on the spine, for example, as is known, by a hook intended to be anchored on a vertebral lamina.

While the inventions have been illustrated and described in detail in the drawings and foregoing description, the same is to be considered as illustrative and not restrictive in character, it being understood that only the preferred embodiments have been shown and described and that all equivalents, changes, and modifications that come within the spirit of the inventions described herein and by the following claims are desired to be protected.

What is claimed is:

1. An apparatus, comprising:
   a rod;
   a spinal fixation member;
   a first connector component including a first head defining a first opening therethrough and an elongated extension, the first head engaging the fixation member in a ball and socket joint arrangement;
   a second connector component including a second head defining a seat to receive the rod and an orifice intersecting said seat to receive the extension; and
   a fastener to fix said extension and said rod in contact with one another in said second head.

2. The apparatus of claim 1, wherein the fixation member includes a spherical head with an extension engageable by tooling, the extension including an upper surface with a spherical shape.

3. The apparatus of claim 1, wherein the fixation member is in the form of a screw to engage a vertebra.

4. The apparatus of claim 1, wherein the first head includes an articulating surface with a concave shape and the fixation member includes an upper surface with a convex shape complementary to the concave shape and being received therein.

5. The apparatus of claim 4, wherein the concave shape and the convex shape are each generally spherical.

6. A method, comprising:
   providing a lateral connector including a first component with a first head and an extension and a second component with a second head defining a seat configured to receive a rod and an orifice intersecting the seat;
   implanting a fixation member in a spine of the patient;
   receiving the fixation member in the first head;
   adjusting position of the first component about the fixation member after said receiving in a first direction of rotational freedom;
   changing position of the first component about the fixation member after said receiving in a second direction of rotational freedom different than the first direction of rotational freedom;
   inserting the extension into the orifice of the second component;
   translationally adjusting distance between the first head and the second head after said inserting;
   rotationally adjusting the second head about the extension after said inserting; and
   fixing the extension and the rod in contact with one another in the second head of the second component.

7. The method of claim 6, removing an end portion of the extension after said inserting.

8. The method of claim 6, further comprising immobilizing the fixation member with respect to the first head after said adjusting and said changing.

9. The method of claim 8, wherein said receiving includes engaging an articulating surface of the first head with a spherical surface of the fixation member and the fixation member includes a tooling extension projecting away from said spherical surface, the tooling extension terminating in a spherically shaped upper surface, and wherein said immobilizing includes threading a plug into an opening of the first head to contact the upper surface of the tooling extension.

10. The method of claim 6, wherein the first head and the fixation member engage one another in a ball and socket joint relationship.

11. The method of claim 6, wherein, said implanting is performed before said receiving.

12. The method of claim 11, wherein the first head includes an opening therethrough intersected by a lateral notch and said receiving includes laterally sliding an upper head portion of the fixation member into the first head through the lateral notch.

13. The method of claim 12, wherein said implanting includes screwing the fixation member into a cervical vertebra of the spine.

14. Lateral connector system for connecting to a rod effective to stabilize the spine, the system comprising:

a fixation member to engage the spine, the fixation member including a fixation member head;

a connector including a first component and a second component, the first component being operable to connect to the fixation member and including: a first head comprising an opening which passes therethrough, an extension having a generally cylindrical shape, and a lower part with a bearing surface of articulation shaped to engage a corresponding bearing surface of the fixation member head with at least two degrees of rotational freedom; the second component including: a second head further comprising a seat for receiving the rod, a fastener, and an orifice formed in the second head for receiving the extension of the first component, the orifice opening into the seat; and wherein the extension and the second component are structured to adjustably insert the extension in translation through the orifice to contact the rod when received in the seat and provide an adjustable rotational position of the second component about the extension when inserted through the orifice, and the fastener fixes the extension and the rod relative to one another when the extension is received through the orifice to contact the rod received in the seat.

15. Connector according to claim 14, wherein the first head comprises a lateral aperture to receive a head of the fixation member.

16. The system of claim 14, wherein an axis of the seat receiving the rod and the orifice receiving the extension of the first component are oriented obliquely in relation to one another.

17. The system of claim 14, wherein the extension comprises an at least partially polygonal section forming longitudinal flats on a lateral surface.

18. The system of claim 14, wherein the extension comprises transverse recesses shaped to match an outer surface of the rod.

19. The system of claim 14, wherein the fastener includes a threaded plug cooperating with a thread formed in the second head, and the second head has two lateral branches delimiting the seat.

20. The system of claim 14, further comprising means for fixing the first component relative to the fixation member, the fixing means including an internally threaded hole in an upper part of the opening of the first head and an externally threaded plug.

* * * * *